(12) United States Patent
Stelzer

(10) Patent No.: US 6,187,582 B1
(45) Date of Patent: Feb. 13, 2001

(54) PROCESS FOR PRODUCING OPTICALLY ACTIVE AMINES

(75) Inventor: Uwe Stelzer, Burscheid (DE)

(73) Assignee: Bayer Aktiengesellschaft, Leverkusen (DE)

(*) Notice: Under 35 U.S.C. 154(b), the term of this patent shall be extended for 0 days.

(21) Appl. No.: 09/194,268
(22) PCT Filed: May 20, 1997
(86) PCT No.: PCT/EP97/02547
 § 371 Date: Nov. 20, 1998
 § 102(e) Date: Nov. 20, 1998
(87) PCT Pub. No.: WO97/46698
 PCT Pub. Date: Dec. 11, 1997

(30) Foreign Application Priority Data

May 30, 1996 (DE) ............................................. 196 21 686

(51) Int. Cl.$^7$ ................................................. C12P 13/00
(52) U.S. Cl. ............................................. 435/280; 435/128
(58) Field of Search .................................. 435/128, 280; 564/213

(56) References Cited

U.S. PATENT DOCUMENTS

| | | | |
|---|---|---|---|
| 4,858,950 | 8/1989 | Kajiwara et al. | 283/719 |
| 4,895,849 | 1/1990 | Yoshioka et al. | 264/241 |
| 4,985,426 | 1/1991 | Yoshioka et al. | 264/241 |
| 4,988,734 | 1/1991 | Kraatz et al. | 341/624 |
| 5,028,256 * | 7/1991 | Martin | 71/118 |
| 5,273,898 | 12/1993 | Ishii | 287/198 |
| 5,668,140 | 9/1997 | Schaper et al. | 519/269 |
| 5,728,876 | 3/1998 | Balkenhohl et al. | 4/136 |

FOREIGN PATENT DOCUMENTS

| | | |
|---|---|---|
| 0 399 589 | 11/1990 | (EP). |
| 0 453 137 | 10/1991 | (EP). |
| 2246774 | 2/1992 | (GB). |
| 91/19002 | 12/1991 | (WO). |

OTHER PUBLICATIONS

Cas Online Printout, 73:87622, Najasawa et al, Feb. 1966.*
Chimia, 48 (month unavailable) 1994, p. 570.
Indian Journal of Chemistry, vol. 32B, Jan. 1993, p. 76–80.
Chemical Abstracts, vol. 115, No. 25, Dec. 1991, Abstract No. 278181.
Chemical Abstract, vol. 115, No. 19, Nov. 11, 1991, Abstract No. 206019.
Tetrahedron: Asymmetry, vol. 7, No. 5, (month unavailable) 1996, pp. 1507–1513.
Quiros, Margarita et al, Tetrahedron: Asymmetry, vol. 4, No. 6, (month unavailable) 1993, pp. 1105–1112.
Database WPI, CH, Wk 9732, Derwent Publications Ltd., JP 09 140 389, (Kawaken Fine Chem Co Ltd, Jun. 3, 1997.

* cited by examiner

Primary Examiner—Samuel Barts
(74) Attorney, Agent, or Firm—Joseph C. Gil

(57) ABSTRACT

The present invention provides a novel process for producing known optically active amines and optically active acylated amines by:

a) in a first step, reacting racemic amines with esters, in the presence of hydrolases and possibly a diluent;

b) in a second step, separating the reaction mixture into (S)-amine and acylated (R)-amine; and c) optionally in a third step releasing (R)-amine from acylated (R)-amine by treatment with an acid or base, possibly in the presence of a diluent.

The optically active amines can be employed as intermediates for preparing pharmaceuticals and crop protection agents.

4 Claims, No Drawings

PROCESS FOR PRODUCING OPTICALLY ACTIVE AMINES

TECHNICAL FIELD OF THE INVENTION

Process for preparing optically active amines The present invention relates to a novel process for preparing known, optically active amines which can be employed as intermediates for preparing pharmaceuticals and crop protection agents. Moreover, the invention relates to novel optically active acylated amines.

BACKGROUND OF THE INVENTION

It is already known from DE-A 4 332 738 that optically active, primary and secondary amines can be prepared by initially enantioselectively acylating racemic amine in the presence of a hydrolase using an ester which has an electron-rich heteroatom in the acid moiety in the vicinity of the carbonyl carbon atom, then separating the resulting mixture of optically active (S)-amine and optically active acylated (R)-amine (=amide), thereby affording the (S)-amine, and obtaining the other enantiomer, if desired, from the acylated (R)-amine by amide cleavage. Suitable hydrolases are lipases from Pseudomonas, for example Amano P, or from Pseudomonas spec. DSM 8246. The degree of optical purity of the enantiomers that are obtained is very high. However, this process has the disadvantages that relatively long reaction times are required for the enzymatic acylation and that the reaction is carried out in highly dilute solution. Only after relatively long reaction times is the remaining (S)-enantiomer obtained in sufficiently high optical yield. For practical purposes, the space-time yields that can be achieved are therefore inadequate. It is a further disadvantage that relatively high amounts of enzyme are required with respect to the substrate. Besides, the enzyme has very high activity, so that purification, concentration and work-up requires considerable effort. Moreover, a relatively expensive acylation component is necessary.

Furthermore, Chimica 48, 570 (1994) discloses that racemic amines will react enantioselectively with ethyl acetate in the presence of lipase from Candida antarctica to give mixtures of (S)-amine and acetylated (R)-amine (=amide) from which (S)-amine and acetylated (R)-amine can be isolated, it being possible to set free the acetylated (R)-amine by subsequent amide cleavage. Disadvantages of this method are that once more relatively long reaction times are required and that furthermore the yields are not always satisfactory. In addition, the ratio of enzyme to substrate is again so disadvantageous that an economical utilization of the process is scarcely possible.

DETAILED DESCRIPTION OF THE INVENTION

It has now been found that optically active amines of the formula

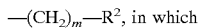

(I*)

in which

R represents alkyl having 1 to 10 carbon atoms, halogenoalkyl having 1 to 10 carbon atoms and 1 to 5 halogen atoms, alkoxyalkyl having 1 to 10 carbon atoms in the alkyl moiety and 1 to 3 carbon atoms in the alkoxy moiety or alkenyl having 2 to 10 carbon atoms, or represents a radical of the formula —(CH$_2$)$_m$—R$^2$, in which R$^2$ represents aryl or aryloxy which is optionally mono- to trisubstituted by identical or different substituents, but where the positions of the aryl group which are adjacent to the linking point do not carry any substituents, or R$^2$ represents optionally benzo-fused heteroaryl which is optionally mono- to trisubstituted by identical or different substituents, but where the positions of the heteroaryl group which are adjacent to the linking point do not carry any substituents, and m represents the numbers 0, 1, 2 or 3, and R$^1$ represents hydrogen or alkyl, are obtained by a) reacting, in a first step, racemic amines of the formula

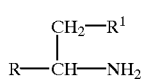

(I)

in which

R and R$^1$ are each as defined above, with esters of the formula

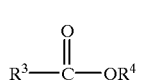

(II)

in which

R$^3$ represents hydrogen, alkyl having 1 to 12 carbon atoms, alkenyl having 2 to 12 carbon atoms, alkinyl having 2 to 12 carbon atoms, halogenoalkyl having 1 to 10 carbon atoms and 1 to 5 fluorine and/or chlorine atoms, or represents a radical of the formula —CH$_2$—C≡N or —(CH$_2$)$_n$—R$^5$, in which R$^5$ represents phenyl which is optionally mono- to trisubstituted by identical or different substituents from the group consisting of halogen, amino, hydroxyl, alkyl having 1 to 4 carbon atoms, alkoxy having 1 to 4 carbon atoms, phenyl and phenoxy and n represents the numbers 0, 1, 2 or 3, or R$^3$ represents a radical of the formula —CH$_2$—COOR$^6$, in which R$^6$ represents alkyl having 1 to 4 carbon atoms, and R$^4$ represents alkyl having 1 to 10 carbon atoms, or represents halogenoalkyl having 1 to 6 carbon atoms and 1 to 5 halogen atoms, where, however, R$^3$ does not represent methyl when R$^4$ represents ethyl, in the presence of hydrolases, if appropriate in the presence of a diluent, b) separating, in a second step, the resulting mixture of (S)-amine of the formula

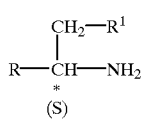

(I-S)

in which

R and R$^1$ are each as defined above, and acylated (R)-amine of the formula

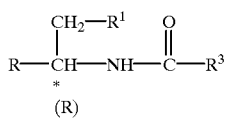

(III)

in which
R, $R^1$ and $R^3$ are each as defined above, and
c) if appropriate, setting free, in a third step, the (R)-amine of the formula

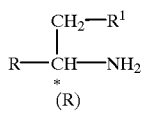

(I-R)

in which
R and $R^1$ are each as defined above, from the acylated (R)-amine of the formula (III) by treatment with acid or base, if appropriate in the presence of a diluent.

(R)-amines are understood to mean those optically active compounds of the formula (I) which exhibit the (R) configuration at the asymmetrically substituted carbon atom. Correspondingly, (S)-amines are understood to mean those optically active compounds of the formula (I) which exhibit the (S) configuration at the chiral centre. In the formulae, the asymmetrically substituted carbon atom is in each case indicated by (*).

It is extremely surprising that optically active amines of the formula (I*) can be prepared in high yield and very good optical purity by the process according to the invention. From the known prior art, it could not be foreseen that an enantioselective amine synthesis is possible even with those esters which do not have an electron-rich heteroatom in the acid moiety in the vicinity of the carbonyl carbon atom. Furthermore, it could not be expected that better results can be obtained by the process according to the invention than by the corresponding reaction using ethyl acetate as acylation component.

The process according to the invention enjoys a number of advantages. Thus, it makes possible the preparation of a large number of optically active amines in high yield and excellent optical purity. It is also favourable that the reaction can be carried out at relatively high substrate concentration and that the reaction times are short. It is therefore possible to achieve space-time yields which are satisfactory even for practical purposes. Furthermore, the acylation components are reasonably priced and readily accessible materials. It is a further advantage that the biocatalyst required is available in relatively large amounts and that it is stable even at elevated temperatures. In terms of the amount of enzyme relative to the substrate, the biocatalyst is employed in a relatively low amount and low enzyme activity. Finally, no difficulties are involved in carrying out the reaction and isolating the desired substances, namely either the (S)- or the (R)-amines.

If racemic 1-(4-chlorophenyl)-ethylamine is reacted with butyl n-acetate in the presence of lipase from Candida antarctica, the resulting components are separated and the (R)-enantiomer of N-[1-(4-chlorophenyl)-ethylacetamide is treated with hydrochloric acid, the course of the process according to the invention can be illustrated by the equation that follows.

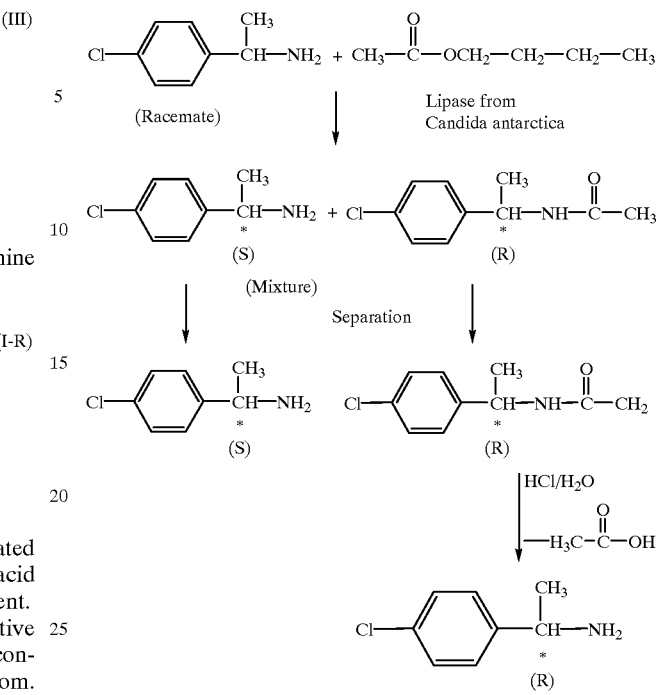

The formula (I) provides a general definition of the racemic amines required as starting materials for carrying out the process according to the invention.

R preferably represents straight-chain or branched alkyl having 1 to 7 carbon atoms, halogenoalkyl having 1 to 5 carbon atoms and 1 to 5 fluorine and/or chlorine atoms, alkoxyalkyl having 1 to 5 carbon atoms in the alkyl moiety and 1 to 3 carbon atoms in the alkoxy moiety, alkenyl having 2 to 8 carbon atoms, or represents a radical of the formula —$(CH_2)_m$—$R^2$, in which $R^2$ preferably represents optionally substituted phenyl of the formula

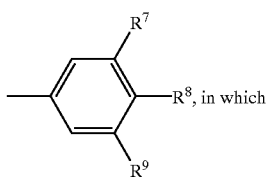

$R^7$, $R^8$ and $R^9$ independently of one another each represent hydrogen, halogen, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, cyano, dialkylamino having 1 to 4 carbon atoms in each alkyl group, nitro, phenyl, phenoxy or benzyl, or $R^2$ represents naphthyl which is optionally mono- to trisubstituted by identical or different substituents from the group consisting of halogen, alkyl having 1 to 4 carbon atoms, halogenoalkyl having 1 to 4 carbon and 1 to 5 identical or different halogen atoms, alkoxy having 1 to 4 carbon atoms, alkylthio having 1 to 4 carbon atoms and halogenoalkoxy having 1 to 4 carbon atoms and 1 to 5 identical or different halogen atoms, but where the positions ortho to the carbon atom through which the naphthyl radical is bonded are unsubstituted, or $R^2$ represents optionally substituted phenoxy of the formula

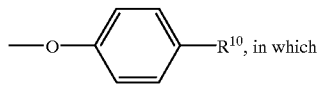

$R^{10}$ represents hydrogen, halogen, alkyl having 1 to 4 carbon atoms, alkoxy having 1 to 4 carbon atoms, alkylthio having 1 to 4 carbon atoms, alkylthio having 1 to 4 carbon atoms, halogenoalkyl having 1 to 4 carbon atoms having 1 to 5 identical or different halogen atoms, cyano, dialkylamino having 1 to 4 carbon atoms in each alkyl group, nitro, phenyl, phenoxy or benzyl, or $R^2$ represents optionally benzo-fused heteroaryl having 5 or 6 ring members and 1 to 3 heteroatoms, such as nitrogen, oxygen and/or sulphur, in the heterocycle, where these radicals may be mono- to trisubstituted by identical or different substituents from the group consisting of halogen, alkyl having 1 to 4 carbon atoms, alkoxy having 1 to 4 carbon atoms and halogenoalkyl having 1 to 4 carbon atoms, but where the positions of the heteroaryl group which are adjacent to the linking point do not carry any substituents, and m also preferably represents the numbers 0, 1, 2 or 3.

$R^1$ preferably represents hydrogen or straight-chain or branched alkyl having 1 to 6 carbon atoms.

In the amines of the formula (I), R and —$CH_2$—$R^1$ in each case represent different radicals.

Particular preference is given to amines of the formula (I) in which

R represents straight-chain or branched alkyl having 1 to 7 carbon atoms, halogenoalkyl having 1 to 5 carbon atoms and 1 to 3 fluorine and/or chlorine atoms, represents alkoxyalkyl having 1 to 3 carbon atoms in the alkyl moiety and 1 to 3 carbon atoms in the alkoxy moiety, alkenyl having 2 to 6 carbon atoms or represents a radical of the formula —$(CH_2)_m$—$R^2$, in which $R^2$ particularly preferably represents optionally substituted phenyl of the formula

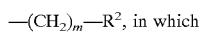

$R^7$, $R^8$ and $R^9$ independently of one another each represent hydrogen, fluorine, chlorine, bromine, methyl, ethyl, n-propyl, isopropyl, n-butyl, iso-butyl, sec-butyl, methoxy, ethoxy, methylthio, trichloromethyl, trifluoromethyl, difluoromethyl, trifluoromethoxy, difluorochloromethoxy, difluoromethoxy, cyano, dimethylamino, diethylamino, nitro, phenyl, phenoxy or benzyl, or $R^2$ represents naphthyl which is optionally mono- to trisubstituted by identical or different substituents from the group consisting of fluorine, chlorine, bromine, methyl, ethyl, n-propyl, isopropyl, n-butyl, iso-butyl, sec-butyl, methoxy, ethoxy, methylthio, trichloromethyl, trifluoromethyl, difluoromethyl, trifluoromethoxy, difluorochloromethoxy and difluoromethoxy, but where the positions ortho to the carbon atom through which the naphthyl radical is bonded are not substituted, or $R^2$ represents optionally substituted phenoxy of the formula

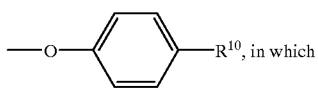

$R^{10}$ represents hydrogen, fluorine, chlorine, bromine, methyl, ethyl, n-propyl, iso-butyl, sec-butyl, methoxy, ethoxy, methylthio, trichloromethyl, trifluoromethyl, difluoromethyl, trifluoromethoxy, difluorochloromethoxy, difluoromethoxy, cyano, dimethylamino, diethylamino, nitro, phenyl, phenoxy or benzyl, $R^2$ represents optionally benzo-fused furyl, thienyl, pyridyl or pyrimidine, where these radicals may be mono- to trisubstituted by identical or different substituents from the group consisting of fluorine, chlorine, bromine, methyl, ethyl, n-propyl, isopropyl, n-butyl, iso-butyl, sec-butyl, tert-butyl, methoxy, ethoxy, n-propoxy, iso-propoxy, trifluoromethyl and trifluoroethyl, but where the positions of the heteroaryl group which are adjacent to the linking point do not carry any substituents, and m represents the numbers 0, 1 or 2, and $R^1$ represents hydrogen, methyl, ethyl, n-propyl or isopropyl.

Examples of racemic amines of the formula (I) include the compounds of the formulae that follow:

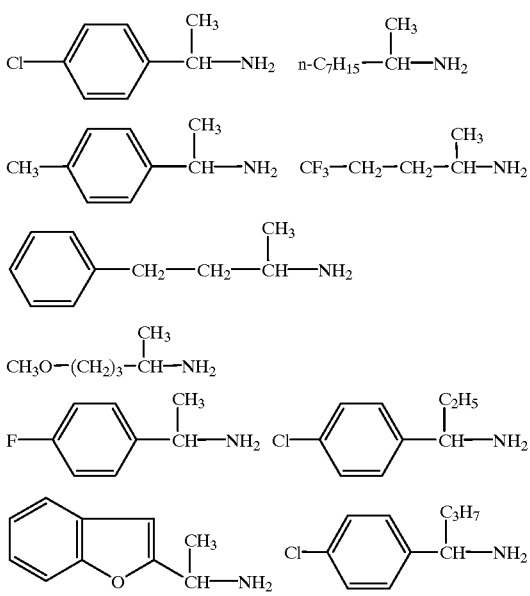

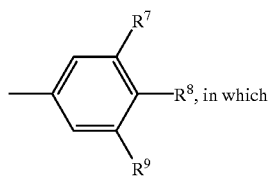

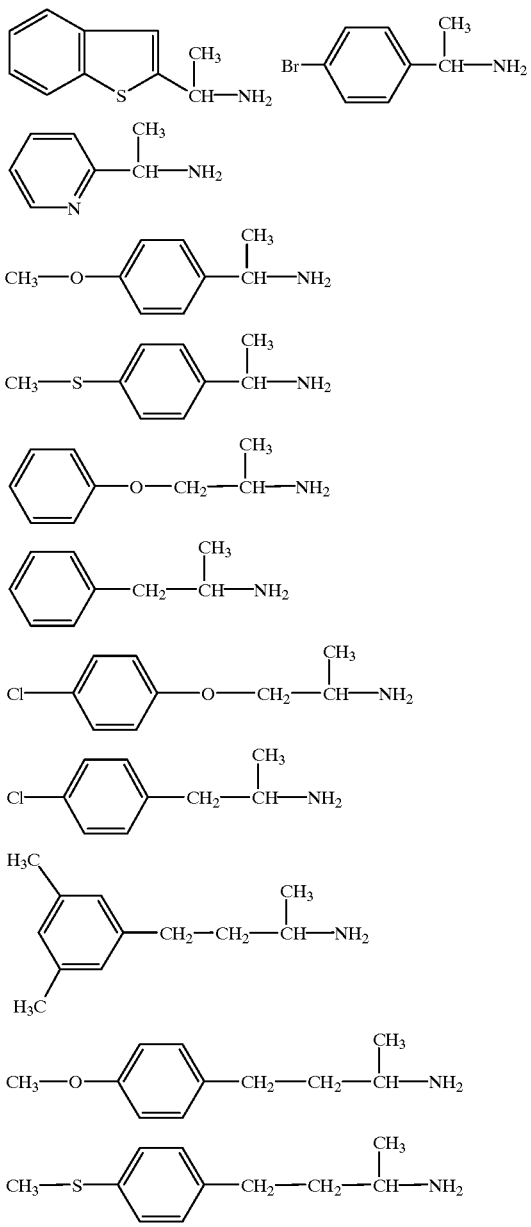

The racemic amines of the formula (1) are known or can be prepared by known methods.

The formula (II) provides a general definition of the esters required as reaction components for carrying out the first step of the process according to the invention.

$R^3$ preferably represents hydrogen, straight-chain alkyl having 1 to 8 carbon atoms, straight-chain alkenyl having 2 to 8 carbon atoms, straight-chain alkinyl having 2 to 8 carbon atoms, straight-chain halogenoalkyl having 1 to 4 carbon atoms and 1 to 3 fluorine and/or chlorine atoms, or represents a radical of the formula —$CH_2$—C≡N or —$(CH_2)_n$—$R^5$, in which $R^5$ represents phenyl which is optionally mono- to trisubstituted by identical or different substituents from the group consisting of fluorine, chlorine, bromine, amino, hydroxyl, methyl, ethyl, methoxy, ethoxy, phenyl and phenoxy and n represents the numbers 0, 1 or 2, or $R^3$ preferably represents a radical of the formula —$CH_2$—$COOR^6$, in which $R^6$ preferably represents methyl, ethyl, n-propyl or n-butyl.

$R^4$ preferably represents straight-chain alkyl having 1 to 8 carbon atoms, or represents straight-chain halogenoalkyl having 1 to 4 carbon atoms and 1 to 3 fluorine and/or chlorine atoms.

Particular preference is given to esters of the formula (11) in which $R^3$ represents hydrogen, methyl, ethyl, n-propyl, n-butyl, vinyl, allyl, propargyl, chloromethyl, fluoromethyl, trifluoromethyl, 2-chloroethyl, or represents a radical of the formula —$CH_2$—C≡N or —$(CH_2)_n$—$R^5$, in which $R^5$ represents phenyl which is optionally mono- or disubstituted by fluorine, chlorine, bromine, amino, hydroxyl, methyl, ethyl, methoxy, phenyl and/or phenoxy and n represents the numbers 0, 1 or 2, or $R^3$ represents a radical of the formula —$CH_2$—$COOR^6$, in which $R^6$ represents methyl, ethyl, n-propyl or n-butyl, and $R^4$ represents methyl, ethyl, n-propyl, n-butyl, chloromethyl, 2-chloroethyl, 2-fluoroethyl or 2,2,2-trifluoroethyl.

In the formula (II), however, $R^3$ does not represent methyl when $R^4$ represents ethyl.

Examples of esters of the formula (II) include the compounds of the formulae that follow.

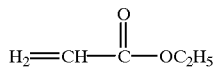
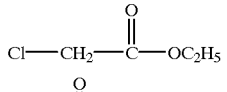
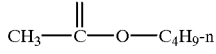
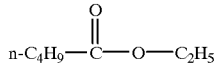
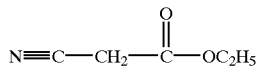
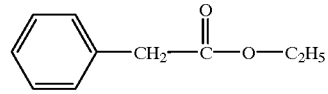
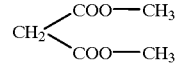

The esters of the formula (II) are known or can be prepared by known methods.

Suitable hydrolases for carrying out the first step of the process according to the invention are lipases and proteases. Preference is given to using lipase from Candida antarctica, lipase from Pseudomonas for example Amano P, and also Subtilisin. Particular preference is given to using lipase from Candida antarctica (=Novozym 435®).

The abovementioned substances are known. Thus, the preparation of lipase from Candida antarchica is described in the literature (cf. Ind. J. Chem. 32B, 76–80 (1993) and EP-A 0 287 634). Lipase from Candida antarctica is commercially available under the name Novozym 435®.

Lipase from Pseudomonas, such as, for example, the product with the name Amano P (=lipase P) or Amano PS (=lipase PS) can be isolated from Pseudomonas cepacia. It is registered under the IUB-No. 3.1.1.3 and is commercially available.

Subtilisin, which is also known as Subtilisin A, can be isolated from

Bacillus licheniformis. It is registered under the IUB-No. 3.4.21.62 and is also commercially available.

The hydrolases can be employed either in native or in modified form, for example microencapsulated or bound to inorganic or organic support materials. Examples of support materials which are suitable in this context are Celite, Lewatit, zeolites, polysaccharides, polyamides and polystyrene resins.

Suitable diluents for carrying out the first step of the process according to the invention are all organic solvents which are customary for such reactions. Preference is given to using ethers, such as methyl tert-butyl ether, dimethoxyethane or tert-amyl methyl ether, furthermore aliphatic or aromatic hydrocarbons, such as hexane, cyclohexane or toluene, additionally nitriles, such as acetonitrile or butyronitrile, moreover alcohols, such as tert-butanol or 3-methyl-3-pentanol, and finally also the esters used for the acylation.

When carrying out the first step of the process according to the invention, the temperatures can be varied within a certain range. In general, the reaction is carried out at temperatures between 0° C. and 80° C., preferably between 10° C. and 60° C.

The first step of the process according to the invention is generally carried out under atmospheric pressure, if appropriate under an inert gas such as nitrogen or argon.

When carrying out the first step of the process according to the invention, generally 0.6 to 10 mol, preferably 1 to 3 mol of ester of the formula (II) are employed per mole of racemic amine of the formula (I). The amount of hydrolase can also be varied within a certain range. In general, 1 to 10% by weight of immobilized hydrolase, based on racemic amine, are employed, corresponding to an activity of 10,000 to 112,000 units of hydrolase per mole of racemic amine. Specifically, the first step of the process according to the invention is carried out in such a manner that the components are added in any order and the resulting mixture is stirred at the particular reaction temperature until the desired conversion has been achieved. To terminate the reaction, the biocatalyst is generally removed by filtration.

In the second step, the mixture obtained in the first step of the process according to the invention is worked up by customary methods. Generally, the desired components are isolated by distillation, fractional crystallization, acid-base solvent extraction or by other means. Thus, it is for example possible to subject the reaction mixture to fractional distillation. It is also possible to concentrate the reaction mixture, to take up the residue that remains in an organic solvent which is sparingly miscible with water, to treat the resulting solution with water and mineral acid and to separate the phases. Concentration of the organic phase affords the acylated (R)-amine. The (S)-amine can be isolated from the aqueous phase by initial treatment with base, subsequent extraction with an organic solvent which is sparingly miscible with water and drying and concentration of the combined organic phases. If appropriate, the isolated products can be purified further, for example by chromatography or distillation. The acylated (R)-amines of the formula

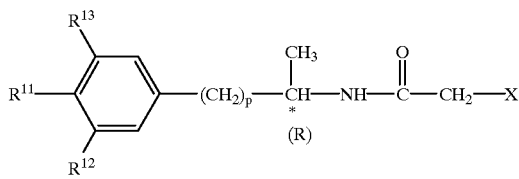

in which $R^{13}$ and $R^{12}$ each represent methyl,
$R^{11}$ represents hydrogen,
p represents the number 2 and
X represents chlorine or cyano, or
$R^{13}$, $R^{11}$ and $R^{12}$ each represent hydrogen,
p represents the numbers I or 2 and
X represents chlorine or cyano, or
$R^{11}$ represents fluorine, chlorine, bromine, methyl, methoxy or methylthio,
$R^{13}$ and $R^{12}$ each represent hydrogen,
p represents the numbers 0, 1 or 2 and
X represents chlorine or cyano, are novel.

Examples of acylated (R)-amines of the formula (IIIa) include the compounds of the following formulae:

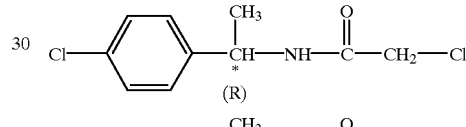

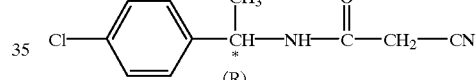

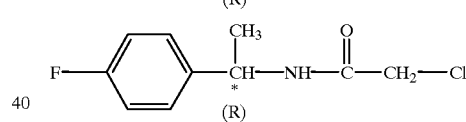

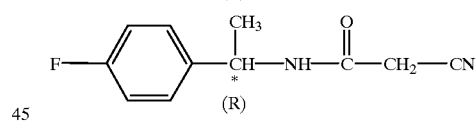

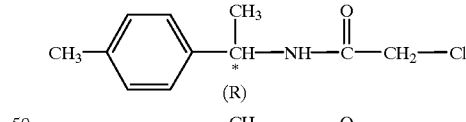

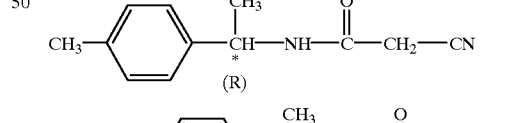

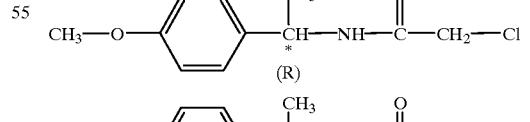

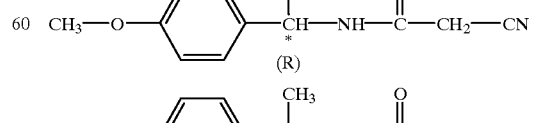

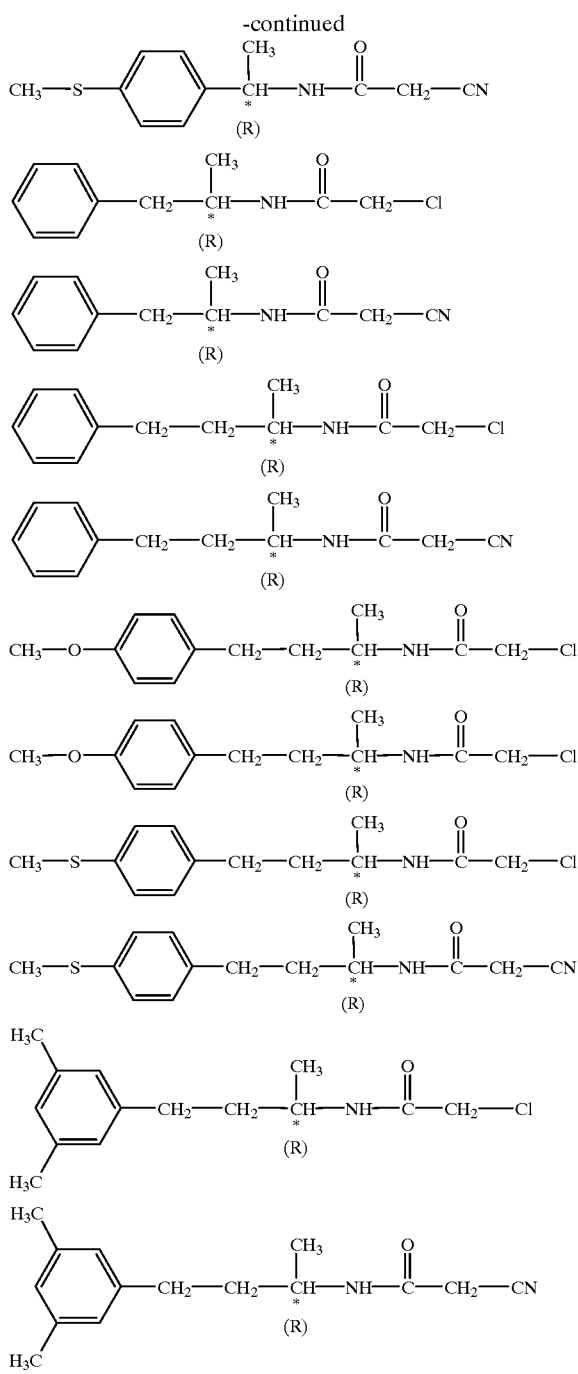

Suitable acids for carrying out the third step of the process according to the invention are all customary strong acids. Those which are preferably utilizable are mineral acids, such as sulphuric acid or hydrochloric acid.

Suitable bases for carrying out the third step of the process according to the invention are all customary strong bases. Those which are preferably utilizable are inorganic bases, such as sodium hydroxide or potassium hydroxide.

Suitable diluents for carrying out the third step of the process according to the invention are all organic solvents which are customary for such reactions, and water. Those which are preferably utilizable are water or mixtures of water and organic solvents, examples including mixtures of water and toluene.

When carrying out the third step of the process according to the invention, the temperatures may be varied within a relatively wide range. In general, the reaction is carried out at temperatures between 20 and 180° C., preferably between 30 and 150° C.

The third step of the process according to the invention is generally carried out under atmospheric pressure. However, it is also possible to work under elevated or reduced pressure.

When carrying out the third step of the process according to the invention, generally 1 to 5 equivalents or else a larger excess of acid or base are employed per mole of acylated (R)-amine of the formula (III). Work-up is carried out by customary methods. In general, after the cleavage has ended and after neutralization, the reaction mixture is extracted with an organic solvent which is sparingly miscible with water, and the combined organic phases are dried and concentrated. If appropriate, the resulting product can be freed from impurities which may still be present using customary methods.

The amines of the formula (I*) preparable by the process according to the invention are useful intermediates for preparing pharmaceuticals or active compounds having insecticidal, fungicidal or herbicidal properties (cf. EP-A 0 519 211, EP-A 0 453 137, EP-A 0 283 879, EP-A 0 264 217 and EP-A 0 341 475). Thus, for example, the fungicidally active compound of the formula (IV)

is obtained by reacting (R)-1-(4-chloro-phenyl)-ethylamine of the formula (I-1)

with 2,2-dichloro-1-ethyl-3-methyl-1-cyclopropanecarbonyl chloride of the formula (V)

in the presence of an acid binder and in the presence of an inert organic diluent.

The examples that follow illustrate the practice of the process according to the invention.

PREPARATION EXAMPLES

Example 1

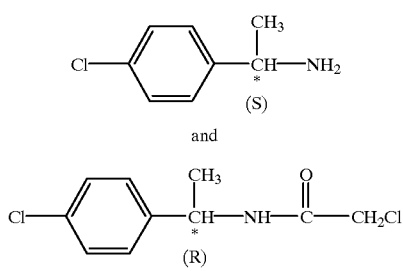

1st Step

At room temperature, a solution of 4.67 g (0.03 mol) of racemic 1-(4-chloro-phenyl)ethylamine in 40 ml of methyl tert-butyl ether is admixed successively with stirring with 5.5 g (0.045 mol) of ethyl chloroacetate and 0.4 g of Novozym 435® (=immobilized lipase from Candida antarctica; 7300 U/g). Stirring is continued at room temperature and the progress of the reaction is monitored by gas chromatographic sample analysis. After 1 hour, a conversion of 51% is reached. At this stage, the reaction is terminated by filtering off the enzyme. In the filtrate that remains, the (S)-enantiomer of 1-(4-chloro-phenyl)-ethylamine has an ee value of 89.1%, while the (R)-enantiomer of N-[1-(4-chloro-phenyl)-ethyl]chloroacetamide is obtained with an ee value of 95.5%.

2nd Step

The filtrate that remains after the enzyme has been filtered off is concentrated under reduced pressure. The residue that is obtained is admixed with 40 ml of a 5% strength aqueous hydrochloric acid and stirred at room temperature for 2 hours. The mixture is extracted three times with methylene chloride. The combined organic phases are dried over sodium sulphate and then concentrated under reduced pressure. In this manner, 3.08 g of a product which, according to gas chromatographic analysis, consists to 95.7% of the (R)-enantiomer of N-[1-(4-chloro-phenyl)-ethyl] chloroacetamide are obtained. The ee value is 97.5%.

Example 2

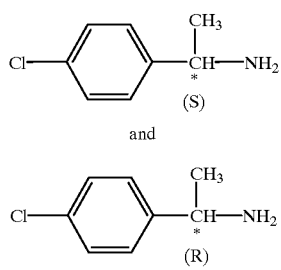

1st Step

At 35° C., a solution of 6.3 g (0.04 mol) of racemic 1-(4-chloro-phenyl)-ethylamine in 45 ml of methyl tert-butyl ether is admixed successively with stirring with 4.9 g (0.04 mol) of ethyl chloroacetate and 0.5 g of Novozym 435® (=immobilized lipase from Candida antarctica; 7300 U/g). Stirring is continued at 35° C. and the progress of the reaction is monitored by gas chromatographic sample analysis. After 4 hours, a conversion of 54% is reached. At this stage, the reaction is terminated by filtering off the enzyme. In the filtrate that remains, the (S)-enantiomer of 1-(4-chloro-phenyl)ethylamine has an ee value of 96.2%, while the (R)-enantiomer of N-[1-(4-chlorophenyl)-ethyl] chloroacetamide is obtained with an ee value of 95.1%.

2nd Step

The filtrate that remains after the enzyme has been filtered off is concentrated under reduced pressure. The residue that is obtained is admixed with 40 ml of a 5% strength aqueous hydrochloric acid and stirred at room temperature for 0.5 hours. The mixture is extracted three times with methylene chloride. The combined organic phases are dried over sodium sulphate and then concentrated under reduced pressure. The residue is admixed with 40 ml of 15% strength aqueous hydrochloric acid and heated under reflux for 3 hours. The reaction mixture is then cooled to room temperature, made basic with aqueous sodium hydroxide solution and extracted repeatedly with methylene chloride. The combined organic phases are dried over sodium sulphate and concentrated under reduced pressure. In this manner, 4.23 g of a product which, according to gas chromatographic analysis, consists to 97% of the (R)-enantiomer of 1-(4-chloro-phenyl)-ethylamine are obtained The ee value is 95.1%.

3rd Step

The aqueous phase which is obtained after the treatment with 5% strength aqueous hydrochloric acid described above is made alkaline by addition of aqueous sodium hydroxide solution and extracted repeatedly with methylene chloride. The combined organic phases are dried over sodium sulphate and then concentrated under reduced pressure. In this manner, 2.38 g of a product which, according to gas chromatographic analysis, consists to 93% of the (S)-enantiomer of 1-(4-chloro-phenyl)-ethylamine are obtained. The ee value is 96.2%.

Example 3

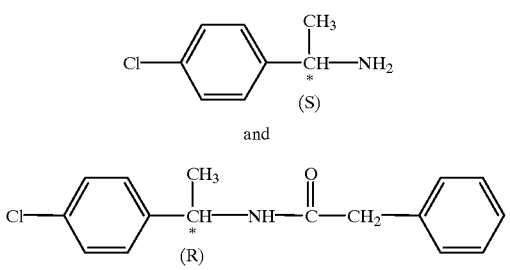

1st Step

At 45° C., a solution of 4.67 g (0.03 mol) of racemic 1-(4-chloro-phenyl)-ethylamine in 40 ml of methyl tert-butyl ether is admixed successively with stirring with 7.38 g (0.045 mol) of ethyl phenylacetate and 0.4 g of Novozym 435® (=immobilized lipase from Candida antarctica; 7300 U/g). The mixture is stirred at 45° C. for a further 8.5 hours and the progress of the reaction is monitored by gas chromatographic sample analysis. After 8.5 hours, a conversion of 40.5% is reached. At this stage, the reaction is terminated by filtering off the enzyme.

2nd Step

The filtrate that remains after the enzyme has been filtered off is concentrated under reduced pressure. The residue that is obtained is admixed with 40 ml of a 5% strength aqueous hydrochloric acid and stirred at room temperature for 2 hours. The mixture is extracted three times with methylene chloride. The combined organic phases are dried over sodium sulphate and then concentrated under reduced pressure. The residue is subjected to silica gel chromatography using petroleum ether/ethyl acetate=2:1 as mobile phase. The eluate is concentrated under reduced pressure, giving 2.85 g of a product which, according to gas chromatographic analysis, consists to 99% of the (R)enantiomer of N-[1-(4-chloro-phenyl)-ethyl]phenylacetamide. The ee value is 98:7%.

$^1$H NMR spectrum (CDCl$_3$/TMS):

δ=1.35 (d, 3H, CH$_3$); 3.55 (s, 2H, CH$_2$); 5.06 (m, 1H, CH); 7.09–7.38 (m, 9H, aromatic protons) ppm.

$[\alpha]_D^{2}$=+112.2°; c 1.06 in the CH$_3$OH

Example 4

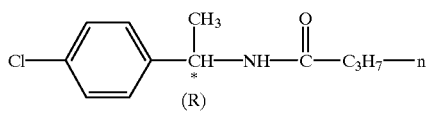

1st Step

At 45° C., a solution of 3.11 g (0.02 mol) of racemic 1-(4-chloro-phenyl)-ethylamine in 30 ml of tert-amyl methyl ether is admixed successively with stirring with 11.6 g (0.1 mol) of ethyl butyrate and 0.3 g of Novozym 435® (=immobilized lipase from Candida antarctica; 7300 U/g). The mixture is stirred at 45° C. for a further 6 hours and the progress of the reaction is monitored by gas chromatographic sample analysis. After 6 hours, a conversion of 43% is reached. At this stage, the reaction is terminated by filtering off the enzyme.

2nd Step

The filtrate that remains after the enzyme has been filtered off is concentrated under reduced pressure. The residue that is obtained is admixed with 40 ml of a 5% strength aqueous hydrochloric acid and stirred at room temperature for 2 hours. The mixture is extracted three times with methylene chloride. The combined organic phases are dried over sodium sulphate and then concentrated under reduced pressure. The residue is subjected to silica gel chromatography using petroleum ether/ethyl acetate=2:1 as mobile phase. The eluate is concentrated under reduced pressure, giving a product which, according to gas chromatographic analysis, consists to 99% of the (R)-enantiomer of N-[1-(4-chloro-phenyl)-ethyl]butyramide. The ee value is 99%.

$^1$H NMR spectrum (CDCl$_3$/TMS):

δ=0.921 (t, 3H, CH$_3$); 1.44 (d, 3H, CH$_3$); 1.64 (m, 2H, CH$_2$); 2.14 (t, 2H, CH$_2$); 5.08 (quintett, H, CH); 5.92 (d, H, NH); 7.21–7.30 (m, 4H, aromatic protons) ppm

Example 5

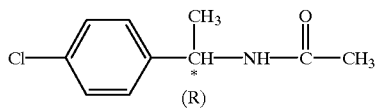

At 45° C., a solution of 3.11 g (0.02 mol) of racemic 1-(4-chloro-phenyl)-ethylamine in 30 ml of tert-amyl methyl ether is admixed successively with stirring with 11.6 g (0.1 mol) of butyl acetate and 0.3 g of Novozym 435® (=immobilized lipase from Candida antarctica; 7300 U/g). Stirring is continued at 45° C. and the progress of the reaction is monitored by gas chromatographic sample analysis. After 4.5 hours, a conversion of 40.9% is reached. At this stage, the reaction is terminated by filtering off the enzyme. In the filtrate that remains, the (R)-enantiomer of N-[1-(4-chloro-phenyl)ethyl]acetamide has an ee value of 99%.

Example 6

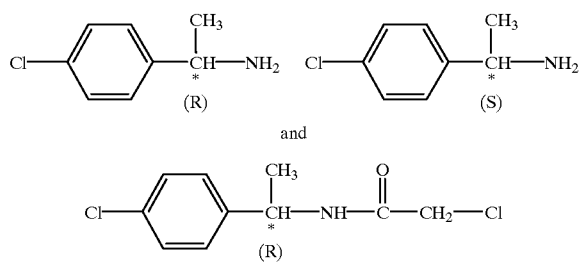

1st Step

At room temperature, a solution of 126.2 g (0.8 mol) of racemic 1-(4-chloro-phenyl)ethylamine in 400 ml of dimethoxyethane is admixed successively with stirring with 98 g (0.8 mol) of ethyl chloroacetate and 6.2 g of Novozym 435® (immobilized lipase from Candida antarctica; 7300 U/g). The mixture is stirred at room temperature for 3 hours and 15 minutes and the reaction is then interrupted by filtering off the enzyme and rinsing with 25 ml of dimethoxyethane.

2nd Step

The filtrate that remains after the enzyme has been filtered off is admixed with 250 ml of ice-water and 68.5 ml (0.8 mol) of concentrated aqueous hydrochloric acid and then concentrated under reduced pressure (40–100 mbar). The mixture is cooled to 5° C. and the precipitated solid is filtered off and rinsed with 150 ml of ice-water. The colourless solid is subsequently dried on clay. In this manner, 85.5 g of a product which, according to gas chromatographic analysis, consists to 99.85% of the (R)-enantiomer of N-[1-(4-chloro-phenyl)-ethyl]chloroacetamide are obtained. The ee value is 99.1%. The calculated yield is 92.1% of theory, $^1$H NMR spectrum (CDCl$_3$/TMS)

δ=1.52 (d, 3H, CH$_3$); 4.05 (d, 2H, CH$_2$); 5.10 (m, 1H, CH); 7.24–7.37 (m, 4H, aromatic protons) ppm The aqueous phase that remains is extracted twice with 100 ml of methylene chloride each time, then admixed with cooling with 100 ml of concentrated aqueous sodium hydroxide solution and reextracted with methylene chloride. The combined organic phases are dried over sodium sulphate and then concentrated under reduced pressure. In this manner, 58.7 g of a product which, according to gas chromatographic analysis, consists to 93.2% of the (S)-enantiomer of 1-(4-chloro-phenyl)-ethylamine are obtained. The ee value is 97.2%. The calculated yield is 88.1% of theory.

3rd Step

A suspension of 85.3 g of the (R)-enantiomer of N-[1-(4-chloro-phenyl)-ethyl]chloroacetamide in 300 ml of water is admixed with 94.5 ml of concentrated aqueous hydrochloric acid and heated under reflux for 18 hours. The mixture is then made alkaline by addition of aqueous sodium hydroxide solution and extracted repeatedly with methylene chloride. The combined organic phases are dried over sodium sulphate and then concentrated under reduced pressure. In this manner, 54.35 g of a product which, according to gas chromatographic analysis, consists to 99.7% of the (R)-enantiomer of 1-(4-chloro-phenyl)-ethylamine are obtained. The ee value is 97.7%. The calculated yield is 87.4% of theory.

The biocatalyst was used in 6 other identical experiments. A loss of activity of 10 to 15% was observed.

Example 7

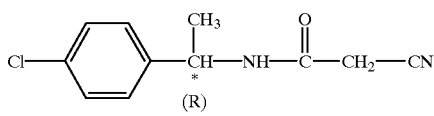

At room temperature, a solution of 6.5 g (0.04 mol) of racemic 1-(4-chloro-phenyl)-ethylamine in 30 ml of ethyl 2-cyano-acetate is admixed with 0.31 g of Novozym 435® (=immobilized lipase from Candida antarctica; 7300 U/g). The mixture is stirred at 40° C. for 3 hours and the reaction is then interrupted by filtering off the enzyme with suction and rinsing with 150 ml of methylene chloride.

The filtrate that remains after the enzyme has been filtered off is admixed with 50 ml of dilute aqueous hydrochloric acid. The organic phase is separated off, dried over sodium sulphate and concentrated under reduced pressure. In this manner, 3.76 g of a product which, according to gas chromatographic analysis, consists to 98.5% of the (R)-enantiomer of N-[1-(4-chloro-phenyl)-ethyl]-2-cyanoacetamide are obtained. The ee value is 95.7%. The calculated yield is 83.4% of theory.

$^1$H NMR spectrum (CDCl$_3$/TMS)

δ=1.52 (d, 3H, CH$_3$); 3.37 (s, 2H, CH$_2$); 5.07 (m, 1H, CH); 6.3 (s, 1H, NH); 7.23–7.35 (m, 4H, aromatic protons) ppm

Example 8

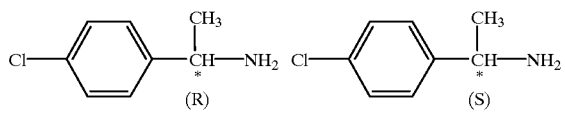

and

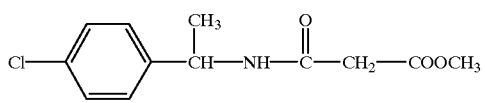

A mixture of 6.2 g (0.04 mol) of racemic 1-(4-chloro-phenyl)-ethylamine, 8.0 g (0.06 mol) of dimethyl malonate, 0.3 g of Novozym 435® (=immobilized lipase from Candida antarctica; 7300 U/g) and 65 ml of dimethoxyethane is stirred at 30° C. for 5 hours. The reaction is then interrupted by filtering off the enzyme with suction.

The filtrate that remains after the enzyme has been filtered off with suction is admixed with 50 ml of 10% strength aqueous hydrochloric acid and then concentrated under reduced pressure. The mixture that is obtained is extracted three times with 50 ml of methylene chloride each time and then made alkaline with concentrated aqueous sodium hydroxide solution. The aqueous phase is repeatedly reextracted with methylene chloride and the combined organic phases are dried over sodium sulphate and cocnentrated under reduced pressure. This gives 2.9 g of a product which, according to gas chromatographic analysis, consists to 95% of the (S)-enantiomer of 1-(4-chlorophenyl)-ethylamine. The ee value is 72%. Yield: 44.8% of theory.

The methylene chloride solution obtained before the treatment with sodium hydroxide solution (first extraction) is concentrated under reduced pressure. This gives a product which essentially consists of the (R)-enantiomer of N-[1-(4-chloro-phenyl-ethyl]methylmalonamide.

$^1$H NMR spectrum (CDCl$_3$/TMS)

δ=1.48 (d, 3H, CH$_3$); 3.35 (s, 2H, CH$_2$); 3.75 (s, 3H, CH$_3$); 5.1 (m, 1H, CH); 7.26–7.29 (m, 4H, aromatic protons) ppm.

The product obtained earlier from the (R)-enantiomer of N-[1-(4-chloro-phenyl)ethyl]methylmalonamide is admixed with 20 ml of half-concentrated aqueous hydrochloric acid and heated under reflux for 9 hours. The mixture is then made alkaline by addition of aqueous sodium hydroxide solution and extracted repeatedly with methylene chloride. The combined organic phases are dried over sodium sulphate and then concentrated under reduced pressure. In this manner, 2.8 g of a product which, according to gas chromatographic analysis, consists to 95% of the (R)-enantiomer of 1-(4-chloro-phenyl)-ethylamine are obtained. The ee value is 93%. The calculated value is 42.8% of theory,

What is claimed is:

1. A process for preparing an optically active amine of the formula

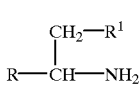

(I*)

wherein

R represents a radical of the formula

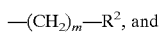

—(CH$_2$)$_m$—R$^2$, and

R$^2$ represents optionally substituted phenyl of the formula

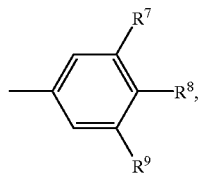

wherein

R$^7$, R$^8$ and R$^9$ independently of one another each represent hydrogen, halogen, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 identical or different halogen atoms, halogenoalkoxy having 1 to 4 carbon atoms and I to 5 identical or different halogen atoms, cyano, dialkylamino having 1 to 4 carbon atoms in each alkyl group, nitro, phenyl, phenoxy or benzyl, and m represents the numbers 0, 1, 2 or 3, and R$^1$ represents hydrogen, comprising the steps of a) reacting in a first step, a racemic amine of the formula (I)

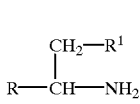

wherein

R and R$^1$ are each as defined above with an ester of the formula

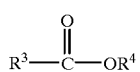 (II)

wherein
R³ represents chloromethyl or a radical of the formula —CH₂—CN, or
R³ represents a radical of the formula —CH₂—COOR⁶, wherein
R⁶ represents methyl, ethyl, n-propyl or n-butyl, and
R⁴ represents methyl, ethyl, n-propyl, or n-butyl, in the presence of lipase from Candida antarctica and in the presence of a diluent, b) separating, in a second step, the resulting mixture of (S)-amine of the formula

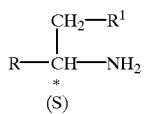 (I-S)

wherein
R and R¹ are each as defined above, and separating the acylated (R)-amine of the formula

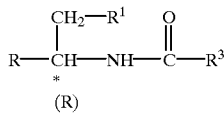 (III)

wherein
R, R¹ and R³ are each as defined above, and c) if appropriate, setting free, in a third step, the (R)-amine of the formula

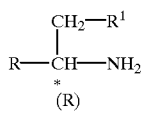 (I-R)

wherein
R and R¹ are each as defined above, from the acylated (R)-amine of the formula (III) by treatment with an acid or a base, if appropriate in the presence of a diluent.

2. Process according to claim 1, characterized in that t he racemic amine of the formula (I) used is 1-(4-chlorophenyl)-ethylamine of the formula

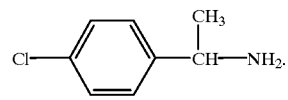

3. Process according to claim 1, characterized in that the ester of the formula (II) used is ethyl chloroacetate of the formula

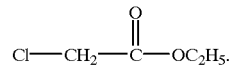

4. Process according to claim 9, characterized in that the first step is carried out at temperatures between 0° C. and 80° C.

* * * * *